(12) United States Patent
Carmeli et al.

(10) Patent No.: US 8,277,469 B2
(45) Date of Patent: Oct. 2, 2012

(54) MULTI-STIFFNESS GUIDEWIRE

(75) Inventors: Ran Carmeli, Rinatya (IL); Jonathan Einav, Raanana (IL); Itai Yonat, Tel Aviv (IL)

(73) Assignee: Eyoca Medical Ltd., Tel Aviv (IL)

( * ) Notice: Subject to any disclaimer, the term of this patent is extended or adjusted under 35 U.S.C. 154(b) by 139 days.

(21) Appl. No.: 12/529,811

(22) PCT Filed: Feb. 28, 2008

(86) PCT No.: PCT/IL2008/000252
§ 371 (c)(1),
(2), (4) Date: Mar. 16, 2010

(87) PCT Pub. No.: WO2008/107869
PCT Pub. Date: Sep. 12, 2008

(65) Prior Publication Data
US 2010/0228151 A1 Sep. 9, 2010

(30) Foreign Application Priority Data
Mar. 7, 2007 (IL) .......................... 181760

(51) Int. Cl.
*A61B 17/22* (2006.01)
*A61D 1/02* (2006.01)
*A61M 25/00* (2006.01)

(52) U.S. Cl. ...................... 606/159; 600/585

(58) Field of Classification Search .......... 600/433, 600/434, 585; 604/164.13, 95.01, 528; 606/127, 606/159, 169
See application file for complete search history.

(56) References Cited

U.S. PATENT DOCUMENTS

| | | | | |
|---|---|---|---|---|
| 5,449,369 A | * | 9/1995 | Imran | ........................... 606/159 |
| 6,423,026 B1 | | 7/2002 | Gesswein et al. | |
| 6,450,975 B1 | | 9/2002 | Brennan et al. | |
| 2003/0105382 A1 | | 6/2003 | Brown et al. | |

FOREIGN PATENT DOCUMENTS

| | | |
|---|---|---|
| DE | 40 36 570 | 5/1992 |
| WO | 94/12234 | 6/1994 |
| WO | 95/04556 | 2/1995 |
| WO | 96/08196 | 3/1996 |
| WO | 2005/092422 | 10/2005 |
| WO | 2006/120674 | 11/2006 |
| WO | 2008/065643 | 6/2008 |

OTHER PUBLICATIONS

International Preliminary Report on Patentability of International Application No. PCT/IL2008/000252, dated Sep. 8, 2009.
International Search Report for corresponding International Application No. PCT/IL2008/000252, dated Jul. 18, 2008.

* cited by examiner

*Primary Examiner* — Rene Towa
*Assistant Examiner* — Jonathan M Foreman
(74) *Attorney, Agent, or Firm* — Tarolli, Sundheim, Covell & Tummino LLP

(57) ABSTRACT

The invention relates to an active oscillating guidewire (26) with varying stiffness to enable a safe crossing through an occluded vessel. The distal working zone (28) is made up of several distal segments (32, 34, 36, 38). A miniature engine is embedded in a segment (34).

13 Claims, 3 Drawing Sheets

MULTI-STIFFNESS GUIDEWIRE

This application is a national phase of International Application No. PCT/IL2008/000252 filed Feb. 28, 2008, and published in the English language under WO 2008/107869 on Sep. 12, 2008.

FIELD OF THE INVENTION

The present invention relates to the field of minimal invasive catheterization. More particularly, the invention relates to a method and device for opening and/or removing obstructions occluding body internal passages by means of an active guidewire. More particularly, the invention relates to an improved active oscillating guidewire with varying stiffness to enable a safe crossing through an occluded vessel.

BACKGROUND OF THE INVENTION

Many vasocclusive events, such as heart attacks and strokes, are caused by plaque build-ups in arteries. As one specific example, atherosclerotic plaque is known to build-up in the walls of arteries in the human body. Such plaque build-up restricts circulation and often causes problems, for example cardiovascular problems, especially when the build-up occurs in coronary arteries.

One common method for opening partially occluded body internal passages is to guide a medical device to the diseased site, where it is used to carry out the needed treatment. A guidewire is usually used for advancing a catheter device thereover via body internal passages towards the treatment site. Typically, the distal tip of the guidewire is introduced into the body of the treated subject via an incision and advanced therethrough towards the treatment site, thereby forming a path leading to the occluded site through said body internal passages. A catheter, or any other suitable treatment devices (e.g., balloon catheter, stent, rotational atherectomy device, laser device etc), may be then threaded over the guidewire and advanced through said internal passages using the guidewire as a rail.

In those cases as described above, regular guidewires are used. These regular guidewires are having a distal tip with low stiffness. The low stiffness is of the order of 1 gram, and therefore is safe for use: it cannot perforate the vessel wall or dissect into the vessel wall. These guidewires are sometimes also called a-traumatic, as they are safe and "gentle" while being threaded via the vessels.

However, sometimes the low stiffness of these guidewires is not sufficient to pass through complicated lesions, such as total or near-total occluded vessels.

Total or near-total occlusions in body internal passages can, partially or entirely, block the passage therethrough. For example, in patients who suffer from coronary chronic total occlusion (CTO), the successful performance of a Percutaneous Transluminal Coronary Angioplasty (PTCA) is a technical challenge. The factor that is most determinative of whether the physician can successfully perform PTCA on patients suffering from coronary CTO is his ability (or inability) to advance a suitable guidewire from a position proximal of the lesion to a position distal of the lesion while remaining inside the true vessel lumen (without performing perforation of the artery wall).

In some instances, such as where the occlusive matter is soft or where the body internal passage is partially occluded, the guidewire can easily be pushed through the occlusive matter itself, thereby allowing the guidewire to remain within the body internal passage. However, in other cases, such as when the body internal passage is totally occluded by hard plaque (e.g., calcified atherosclerotic plaque), the guidewire cannot cross the occlusion and may deviate to the side and penetrate through layers of the passage walls (e.g., the intima—inner layer of a vessel wall), thereby creating a neo-lumen therethrough (e.g., through the sub-intimal space—within the wall of the artery between the intima and media, or adventitia i.e. a dissection), or even completely exit said internal passage i.e. perforate the passage wall.

To enable the treatment of these complicated cases in general, and more particularly Chronical total occlusions (CTO) cases, special guidewires have been developed and introduced into market.

Such guidewires for treating CTO are generally built such that the distal portion of the guidewire is stiffer than that of a regular guidewire. This higher stiffness results in a better penetration capability into hard/calcified tissues in general and totally occluded vessels in particular. Yet, this increased stiffness, often tends to increase the risk of using them, as they can perforate the vessel wall.

The way a physician, is handling a guidewire is by manipulating the guidewire from its proximal side, i.e. from the side outside the body of the patient.

The manipulation is a combination of pushing/pulling and rotating the guidewire until it passes the partially or totally occluded zone.

When using any guidewire, including those with high stiffness, the physician has limited control over the guidewire, as he is manipulating it only from its proximal end.

The configuration of the guidewire, together with the way the physician is manipulating the guidewire, sets a limit in the performance of the said guidewire, i.e. if a physician is selecting a regular stiffness guidewire, this selection, although, will not be suitable for CTO cases. In other cases when the physician selects a high stiffness guidewire, he may be able to pass through a CTO however the risk of using such a guidewire is significantly higher, for the reasons set out above.

Currently there is no guidewire available which enables the physician to change its stiffness depending on the kind of lesion he is trying to cross while the guidewire is already threaded into the vessel. Moreover, there is no guidewire available that inherently can cross a CTO in a safe manner, due the need for new manipulations the physician is required to carry out in addition to the already existing ones.

It would be desirable to have a guidewire with more than a single stiffness zone, providing the physician with:

The capability to select the stiffness of the guidewire during the procedure, while the guidewire is already threaded into the vessel.

Manipulating the guidewire in its high stiffness mode, with an additional new mode of operation/manipulation that is inherently safe to the vessel wall and still capable of crossing CTO's.

It is an object of the present invention, to provide a method and device for opening occluded body internal passages and of body organs, by providing a guidewire comprising at least two zones of different stiffness levels.

SUMMARY OF THE INVENTION

Guidewires are a great technical and clinical challenge. The structure of the guidewire, and generally speaking composition of materials and dimensions of the different segments of the guidewire set the guidewire characteristics. More specifically, most of the guidewire are built in a way that their distal portion (typically the distal 100-300 mm) are made of a special shaped/tapered core, wrapped with a special spring like coil. This coil, together with the inner shaped core of the guidewire, influences dramatically the stiffness of the guidewire, behavior and characteristics.

According to the present invention, the weakest stiffness portion of the guidewire will not be at the most distal portion of the guidewire, but rather proximally to this portion. The most distal portion of the guidewire will then have a higher stiffness level.

An active engine, capable of providing longitudinal force is implemented in between the weakest stiffness portion of the guidewire and the most distal portion of the guidewire.

When a physician is manipulating the guidewire from its proximal end, the guidewire is will perform similarly as common single stiffness guidewire, with the result that the physician cannot apply a pushing force which is higher than the weakest portion of the guidewire.

However, when the physician needs to penetrate a hard/calcified occlusion, he then activates the engine that is pushing the distal portion of the guidewire internally, hence not limited by the weakest portion of the guidewire, and capable of reaching the higher level of stiffness of the guidewire.

It is a further object of the present invention to provide alternatives for internal engines, to be added to the invented guidewire between the distal portion and the weakest portion.

The present invention is directed to a multi-stiffness guidewire structure.

In an embodiment according to the present a guide wire having a distal portion is divided into several segments as listed below:

The most distal segment is designed to have a stiffness level X.

The segment of the guidewire preceding this distal segment is designed to carry an internal engine.

The third segment preceding this second portion is designed to have a stiffness level Y, which is lower then stiffness level X.

Additional segments may precede the said third segment, with either space for a further internal engine or with a stiffness which may be of yet a different level Z.

In another embodiment of the present invention, the guidewire comprises dual stiffness segments follow:

The most distal segment is designed to have a stiffness level X. X is preferably designed to be in the range of 3 to 12 grams The segment of the guidewire preceding this distal segment is designed to carry an internal engine.

The third segment preceding this second portion is designed to have a stiffness level Y. Y is preferable designed to be approximately 1 gram.

In yet another preferred embodiment of the present invention, the dual stiffness guidewire comprises a distal portion of a length range of 50 to 400 mm. This distal portion is constructed of an inner core wrapped with a coil. The shape and dimension of the inner core sets the stiffness of the said guidewire. Accordingly, the preferred embodiment comprises of the following structure:

First segment: The most distal portion of the guidewire comprises an inner core shape suitable to penetrate CTOs with a stiffness of 3-12 grams.

Second segment: At a distance of typically 50-100 mm, the internal engine is added. Since the same inner core is used, it will have the same stiffness of the most distal portion of the guidewire Third segment: Preceding that second segment, the inner core tapers to a lower diameter than that of the second segment, designed to have a stiffness of typically 1 gram.

Forth segment: preceding that third segment, the inner core tapers to a larger diameter to provide a high stiffness segment, typically higher than the stiffnesses of all preceding segments and setting the stiffness of the guidewire.

Preceding that fourth segment, the inner core continues all the way to the proximal side of the guidewire.

In yet another preferred embodiment of the present invention, the engine provided in the second segment comprises magnetic beads added to the guidewire, housed in a coiled support catheter. A more detailed description of this optional engine appears in copending application PCT/2006/000541.

In a further preferred embodiment of this invention the engine added to the guidewire comprises of embedded coils that are part of the guidewire, housed in a support catheter having magnetic beads. A more detailed description of such an optional engine appears in copending Israel patent application 179618.

In alternative configurations of this invention, the second segment may be designed for both carrying the internal engine, as well as being designed to provide the guidewire with its weaker stiffness portion.

This basic structure of the guidewire can be repeated several times, thus providing a guidewire with several levels of stiffnesses.

Thus the present invention provides guidewire for inducing in-vivo vibrations in a body passageway or an organ, comprising:

distal and proximal portions, the distal portion being connected to the proximal portion;

the distal portion comprising at least two segments each having a different stiffness, the most distal segment having a stiffness higher than the segment preceding it; and a miniature engine embedded in a segment connecting said two segments.

All of the above mentioned parameters are given by way of example only, and may be changed in accordance with the different requirements of the various embodiments of the present invention. Thus, the abovementioned parameters should not be construed as limiting the scope of the present invention in any way. In addition, it is to be appreciated that the different wires, inner cores, and other members, described hereinabove may be constructed in different shapes (e.g. having oval, square etc. form in plan view) and sizes differing from those exemplified in the preceding description.

The above examples and description have been provided only for the purpose of illustration, and are not intended to limit the invention in any way. As will be appreciated by the skilled person, the invention can be carried out in a great variety of ways, employing more than one technique from those described above, all without exceeding the scope of the invention.

DETAILED DESCRIPTION OF PREFERRED EMBODIMENTS

Figure 1A:
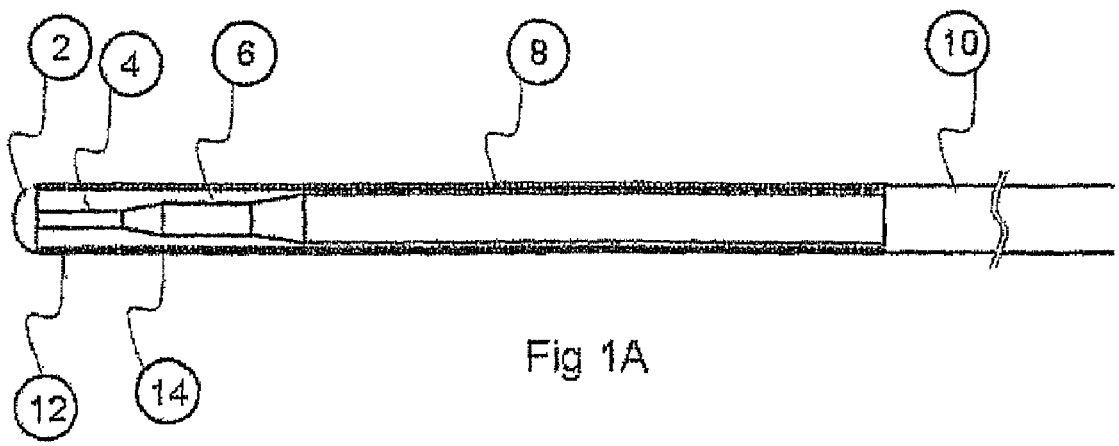
FIG. 1A shows the general structure a prior art guidewire.

FIG. 1A shows a typical guidewire taken from the prior art.

Generally speaking the guidewire is divided into 2 main zones.

Working zone 8, which is eventually inserted bare into the human body vessel, and the rest of the guidewire 10, which in most cases does not touch the vessels, walls, as it is typically housed in a catheter. The overall length of typical guidewires varies in the range of from about 160 to about 300 cm. The working zone 8 is divided into several segments. The front or distal tip of the guidewire 2 is the first part of the guidewire that touches the organ, and must be designed in a way so as to not harm the organ or vessel wall. A core member 4 precedes the distal tip of the guidewire, encased by a spring type envelope 12. The segment set by the core member 4, is typically the flexible zone of the guidewire enabling it to safely and conveniently propagate thru the vessel. This core member 4 sets also the stiffness level of the said guidewire. Typically a second, thicker core member 6 precedes the first core member 4, forming a less flexible zone, also called "stent zone". This member 6 then is connected to the last core member, which is an even thicker and stronger core, used to enable the pushing and steering of the guidewire along and inside the vessel. Some guidewires may different numbers of zones and thus different numbers of core members of varying thickness than described in this figure, so as to fit special clinical needs. The core members may be encased by spring type coils 12, which in turn may be coated with special coatings, such as hydrophilic coating 14.

Figure 1B:
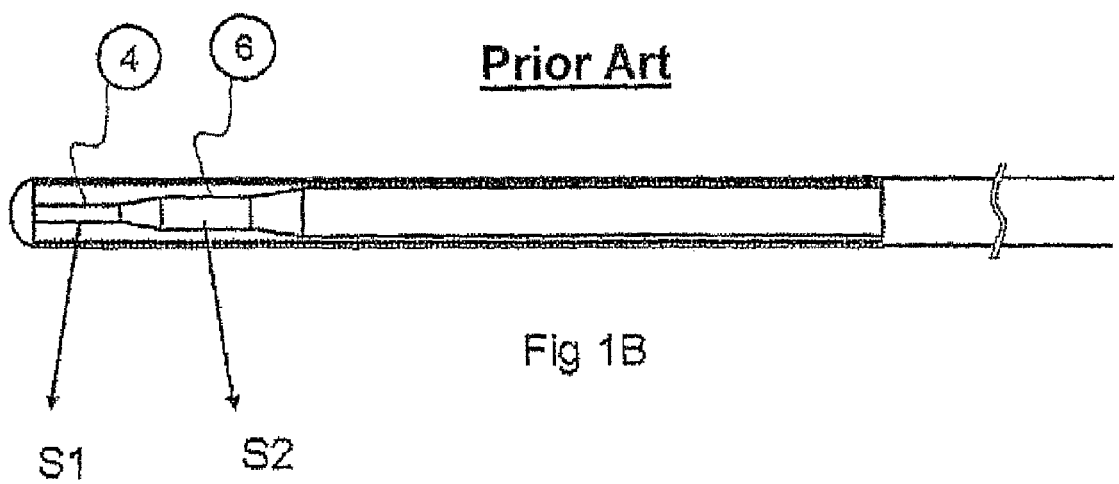
FIG. 1B illustrates the stiffnesses supported by a prior art guidewire at different segments.

FIG. 1B shows the same prior art guidewire. Core member 4 has the lowest stiffness level designated as S1. The member 6 preceding the said first segment 4 has a stiffness designated as S2. In such a known guidewire S1 is lower than S2.

FIG. 2, describes two alternative embodiments according to this invention.

Figure 2A:
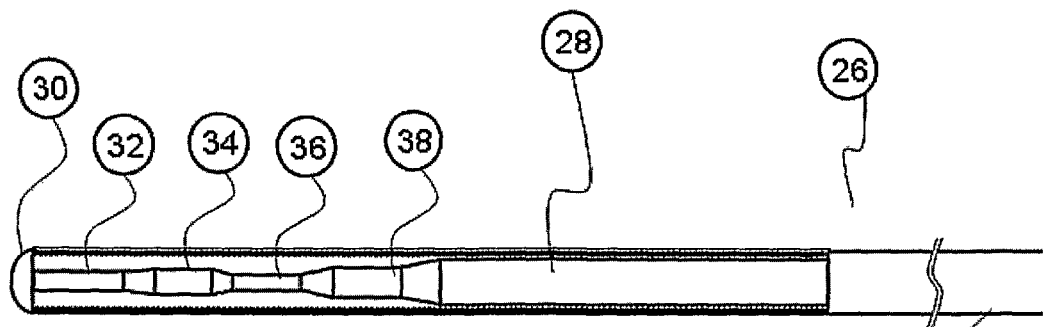
FIG. 2A shows a preferred embodiment of a dual stiffness structure guidewire according to the invention.

In FIG. 2A guidewire 26 comprises a distal working zone 28, and a proximal side 24, of the guidewire. The distal working zone 28 is made up of several distal segments. The most distal segment is the tip 30 of the guidewire. This tip is connected to the front distal core member 32 of the guidewire. This segment has a stiffness designated with S3. Preceding that segment is the miniature engine segment 34. The stiffness the segment that carries the miniature engine may be designed to be of different levels, by controlling the shape and dimensions of the core member of this segment. However in general it would be a relatively high stiffness, designated as S4. Preceding the engine segment 34, there is the weakest stiffness segment 36, with a stiffness level designated as S5. This segment 36 is preceded by the stent segment 38, with a typically higher stiffness level than all previous segments. The stiffnesses of the different segments according to this invention obey the rule that S3 is stiffer than S5. Having these 2 stiffness zones, the guidewire can be designed to suit complicated clinical applications, such as CTOs. The S3 level is typically designed to be in the range of 3-12 grams. The S5 level is typically designed to be in the range of 1 to 3 grams. When the physician is manipulating the guidewire from its proximal side 24, he cannot apply a force bigger than S5, hence the guidewire is safe. When reaching a complicated clinical case, such as CTO, the physician can remotely operate the miniature engine (not shown in this figure) that is embedded into the engine segment 34, hence producing a distal force that can reach the level of S3. The miniature engine may be of the type disclosed in copending patent PCT/IL2006/000541 and/or copending Israeli patent application number IL179618.

Figure 2B:
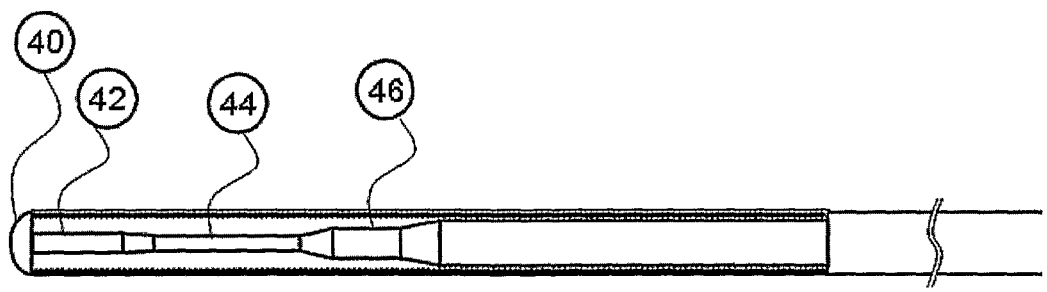
FIG. 2B shows another embodiment of a dual stiffness structure guidewire according to the invention.

FIG. 2B shows an alternative embodiment according to this invention. The guidewire is built in a similar way to the guidewire shown in FIG. 2A, however the distal section comprises only 3 segments: The first segment 42 is a front segment with stiffness level designated as S10, preceded by the weakest segment 44 with stiffness level designated as S11, which also serves as the segment for implementing the miniature engine, and preceded by the stent segment 46. In this embodiment, as in the one shown in FIG. 2A, the physician is manipulating the guidewire from it proximal side, hence cannot produce a force with stiffness larger than S11 which is the stiffness of the weakest segment 44. However if the physician selects to remotely operate the miniature engine embedded in segment 44, he can reach a stiffness level limited by the stiffness S10, which is the stiffness level of the front distal segment 44.

It should be noted, that it is possible to build the guidewire according to the invention in different configurations with different stiffnesses and more segments than shown in FIGS. 2A and 2B.

Figure 3A:
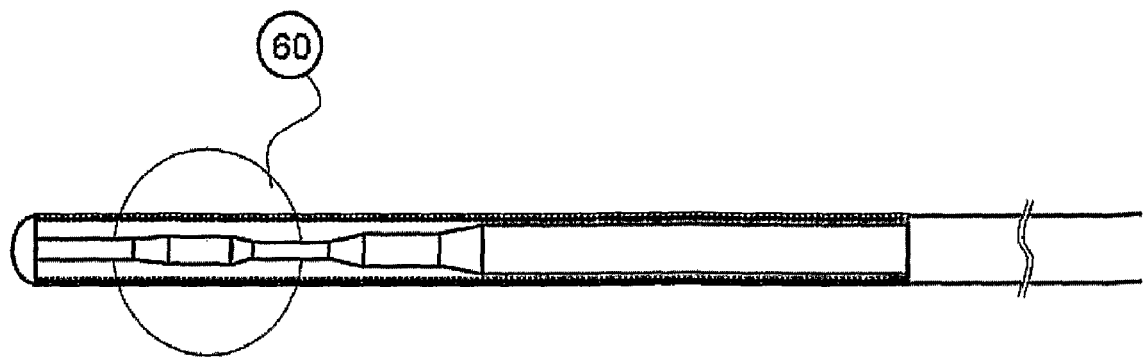
FIG. 3A shows an area of interest where alternatives of engines can be implemented.

FIG. 3A shows a close up view 60 on the engine segment of a guidewire according to this invention.

Figure 3B:
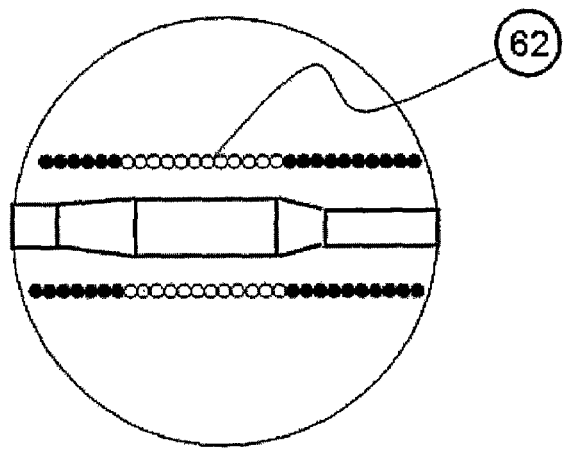
FIGS. 3B and 3C show different type of miniature engines assembled in the middle section of a guidewire according to the invention.

FIG. 3B shows a guidewire where at least part 62 of the coil wrapped around the distal tip is active and can produce magnetic flux. This flux when put in a magnetic field gradient, creates a force working on this section. A detailed description of such engine can is given in copending Israeli patent number IL179618.

Figure 3C:
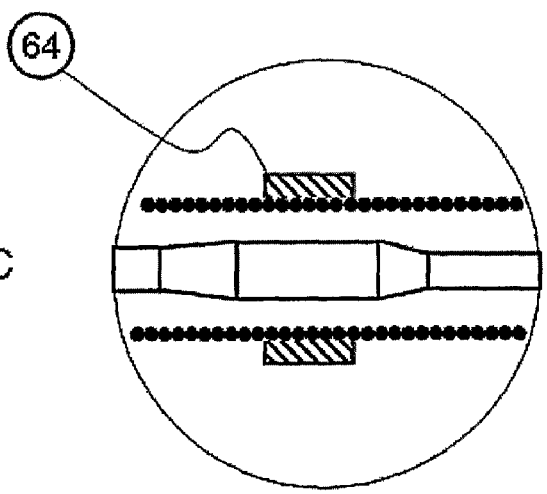

FIG. 3C shows another embodiment of an embedded miniature engine. The engine in this configuration is made of small magnetic beads 64 attached radially to the guidewire. When this magnet bead is put in a magnetic field gradient, a force is developed. A detailed description of such miniature engines is given in copending PCT patent application number PCT/2006/000541.

It should be mentioned, that other miniature engines that can be operated remotely form the proximal side of the guidewire may be implemented, and the configurations of the guidewire also cover these options.

All of the above described parameters are given by way of example only, and may be changed in accordance with the different requirements of the various embodiments of the present invention. Thus, the abovementioned parameters should not be construed as limiting the scope of the present invention in any way. In addition, it is to be appreciated that the different wires, segments, magnets, and other members, described hereinabove may be constructed in different shapes (e.g. having oval, square etc. form in plan view) and sizes differing from those exemplified in the preceding description.

The above examples and description have of course been provided only for the purpose of illustration, and are not intended to limit the invention in any way. As will be appreciated by the skilled person, the invention can be carried out in a great variety of ways, employing more than one technique from those described above, all without exceeding the scope of the invention.

The invention claimed is:

1. A device for inducing in-vivo vibrations in a body passageway or an organ, comprising:
   a guidewire for inducing in-vivo vibrations in a body passageway or an organ, comprising:

a distal working zone and a proximal side, the distal working zone being connected to the proximal side;

the distal working zone comprising a distal tip, a front segment, an engine segment, a weakest segment, and a stent segment;

the distal tip is connected to the front segment, the front segment is preceded by the engine segment, the engine segment is preceded by the weakest segment, and the weakest segment is preceded by the stent segment;

the stiffness of the front segment is greater than the stiffness of the weakest segment;

the engine segment includes an embedded engine, the embedded engine comprising at least one magnetic element, wherein the magnetic element is an active electromagnetic coil;

when the at least one magnetic element is acted on by a magnetic field gradient, a longitudinal force is developed on the engine segment; and a support catheter having permanent magnet beads;

wherein the guidewire is housed in the support catheter and the embedded engine is remotely operable from the proximal side of the device.

2. A device according to claim 1, wherein the operation of the embedded engine causes the guidewire to vibrate, and the amplitude and frequency of the vibrations caused by the embedded engine are remotely controllable from the proximal side of the device.

3. A device according to claim 1, wherein the guidewire maximum pushing force is limited by the stiffness of the weakest segment when the embedded engine is not activated; and wherein the guidewire is not limited by the stiffness of the weakest segment when the embedded engine is activated.

4. A device according to claim 1, wherein the stiffness of the weakest segment is about 1 gram, and the stiffness of the front segment is 3 to 12 grams.

5. A device according to claim 1, wherein the weakest segment has a stiffness level that is not capable of perforating vessel walls and is not capable of dissecting into vessel walls; and the front segment has a stiffness level that is capable of penetrating chronic total occlusions.

6. A device according to claim 5, wherein the distal working zone has a length of 50 mm to 400 mm, and the engine segment is spaced 50 mm to 100 mm from the distal tip of the guidewire.

7. A device for inducing in-vivo vibrations in a body passageway or an organ, comprising:

a guidewire for inducing in-vivo vibrations in a body passageway or an organ, comprising:

a distal working zone and a proximal side, the distal working zone being connected to the proximal side;

the distal working zone comprising a distal tip, a front segment, an engine segment, a weakest segment, and a stent segment;

the distal tip is connected to the front segment, the front segment is preceded by the engine segment, the engine segment is preceded by the weakest segment, and the weakest segment is preceded by the stent segment;

the stiffness of the front segment is greater than the stiffness of the weakest segment;

the engine segment includes an embedded engine, the embedded engine comprising at least one magnetic element, wherein the magnetic element is a permanent magnet;

when the at least one magnetic element is acted on by a magnetic field gradient, a longitudinal force is developed on the engine segment; and a support catheter having active electromagnetic coils;

wherein the guidewire is housed in the support catheter, and the embedded engine is remotely operable from the proximal side of the device.

8. A device according to claim 7, wherein the operation of the embedded engine causes the guidewire to vibrate, and the amplitude and frequency of the vibrations caused by the embedded engine are remotely controllable from the proximal side of the device.

9. A device according to claim 7, wherein the guidewire maximum pushing force is limited by the stiffness of the weakest segment when the embedded engine is not activated; and wherein the guidewire is not limited by the stiffness of the weakest segment when the embedded engine is activated.

10. A device according to claim 7, wherein the stiffness of the weakest segment is about 1 gram, and the stiffness of the front segment is 3 to 12 grams.

11. A device according to claim 7, wherein the weakest segment has a stiffness level that is not capable of perforating vessel walls and is not capable of dissecting into vessel walls; and the front segment has a stiffness level that is capable of penetrating chronic total occlusions.

12. A device according to claim 7, wherein the distal working zone has a length of 50 mm to 400 mm, and the engine segment is spaced 50 mm to 100 mm from the distal tip of the guidewire.

13. A device according to claim 7, wherein the permanent magnet is shaped in the form of a hollow cylinder.

* * * * *